United States Patent [19]

Hijiya et al.

[11] Patent Number: 5,629,450

[45] Date of Patent: May 13, 1997

[54] ADDITION SALT OF ACYL-AMINO ACID AND α-ARYL AMINE AND PROCESS FOR OPTICAL RESOLUTION OF α-ARYLAMINE

[75] Inventors: Toyoto Hijiya; Teruo Yonekawa; Tadashi Takemoto, all of Kawasaki, Japan

[73] Assignee: Ajinomoto Co., Inc., Tokyo, Japan

[21] Appl. No.: 407,844

[22] Filed: Mar. 21, 1995

[30] Foreign Application Priority Data

Jun. 21, 1994 [JP] Japan .................................. 6-139112

[51] Int. Cl.$^6$ ................................................. C07C 209/00
[52] U.S. Cl. ........................... 564/425; 560/157; 560/163; 562/430
[58] Field of Search ..................... 564/387, 392, 564/425

[56] References Cited

U.S. PATENT DOCUMENTS 3,028,430  4/1962  Gillingham .

FOREIGN PATENT DOCUMENTS 06-107604  4/1994  Japan .

OTHER PUBLICATIONS

Patent Abstracts of Japan, vol. 18, No. 385 (C–1227), Jul. 20, 1994, JP-A-06 107604, Apr. 19, 1994.

Organic Synthesis, vol. 49, pp. 93–98, 1969, Ault, "R(+)– and S(–)–α–Phenylethylamine".

*Primary Examiner*—Michael L. Shippen
*Attorney, Agent, or Firm*—Oblon, Spivak, McClelland, Maier & Neustadt, P.C.

[57] ABSTRACT

To produce optically active α-arylalkylamine from optically impure α-arylalkylamine.

Optically impure α-arylalkylamine is mixed with optically active N-acyl-aspartic acid or glutamic acid in a solvent and the resulting two types of diastereomer salts are optically resolved utilizing difference in solubility.

2 Claims, No Drawings

ADDITION SALT OF ACYL-AMINO ACID AND α-ARYL AMINE AND PROCESS FOR OPTICAL RESOLUTION OF α-ARYLAMINE

BACKGROUND OF THE INVENTION

1. Field of the Invention

The present invention relates to an addition salt of an optically active acyl-amino acid and an optically impure α-arylamine, and a method of optical resolution using same.

2. Discussion of the Background

Optically active α-arylalkylamines are important materials as optical resolution agents to obtain optically active substance from a racemic carboxylic acid. Among them, amines wherein the aryl group is phenyl and the alkyl group is methyl or ethyl have been extensively used as optical resolution agents. Further, amines wherein the aryl group is phenyl or methyl-substituted phenyl and which is an S-isomer are important as a raw material for high-potency sweeteners disclosed in U.S. Pat. No. 5,286,509.

To obtain an optically active α-arylakylamine from an optically impure mixture by optical resolution, a method is, generally used wherein salts with various optically active carboxylic acids are formed and the resulting two diastereomeric salts are separated utilizing differences in solubility. Several methods are known, for example, a method utilizing optically active tartaric acid or malic acid (J. Chem. Soc., 1940, 336), a method utilizing optically active N-acetyl-3,5-dibromo-tyrosine (J. Am. Chem. Soc., 73, 5782 (1951)), a method utilizing optically active 2-benzamidocyclohexanecarboxylic acid (Bull. Chem. Soc. Jpn., 61, 1395 (1988)).

However, such methods utilizing tartaric acid or malic acid have poor optical purification ability, and the resulting diastereomeric salts should be repeatedly crystallized for purification. While tartaric acid and malic acid are relatively cheap, they are difficult to recover efficiently from such separation operation, which becomes a problem for industrialization.

The production of optically active N-acetyl-3,5-dibromo-tyrosine has the drawbacks of involving troublesome operations and has poor optical purification ability.

When optically active 2-benzamidocyclohexanecarboxylic acid is used, an amine of high optical purity may be obtained by a single operation of crystallization. However, crystallization yields are not so high. Further, this material is relatively expensive.

From these reasons, while the conventionally known resolution agents are excellent on a laboratory scale, there are some problems of application on an industrial scale.

The problem addressed by the invention is to develop an industrial process to produce, efficiently and at a low cost, optically active α-arylalkylamines from optically impure α-arylalkylamines by optical resolution.

The present inventors have studied intensively to solve the above problems. Surprisingly, we have found that optically active N-acyl-aspartic acid (aspartic acid is hereinafter abbreviated to Asp) and optically impure α-arylalkylamine are mixed in a suitable solvent to give a salt of the optically active N-acyl-Asp and equimolar optically active e-arylalkylamine separated out. Further, we have found that similar optical resolution effect is obtained for optically active N-acyl-glutamic acid (glutamic acid is hereinafter abbreviated to Glu). Thus, we have attained the present invention.

SUMMARY OF THE INVENTION

According to one embodiment of the present invention, an optically impure α-arylalkylamine and an optically active N-acyl-Asp (or Glu) are mixed in a suitable solvent to give two diastereomeric salts, that is:

(i) a salt of the R-amine and the optically active N-acyl-Asp (or Glu); and (ii) a salt of the S-amine and the optically active N-acyl-Asp (or Glu).

These diastereomeric salts are separated by optical resolution, i.e., crystallized utilizing difference in solubility to remove a less soluble one, then the salt is, for example, treated with alkali to readily produce the objective optically active α-arylalkylamine of high purity. Accordingly, production of optically active α-arylalkylamine can be extremely advantageously conducted on an industrial scale.

DETAILED DESCRIPTION OF THE INVENTION

The examples of the solubility of the diastereomer of the salts of optically active N-acyl-Asp or Glue and optically active α-arylalkylamines obtained according to the present invention are shown in Table 1.

TABLE 1

| N-Acyl-amino acid· α-arylalkylamine | Solubility in water*) |
| --- | --- |
| Bz-L-Glu· (S)-α-phenylethylamine | 0.94 |
| Bz-L-Glu· (R)-α-phenylethylamine | 3.69 |
| Z-L-Asp· (S)-α-phenylpropylamine | 0.22 |
| Z-L-Asp· (R)-α-phenylpropylamine | 1.46 |

*)The amount of amine (g) in 100 ml of a saturated solution at 25° C.

The acyl group of the optically active N-acyl-Asp or Glu of the present invention may include, for example, benzyloxycarbonyl, benzoyl, benzenesulfonyl, p-toluenesulfonyl (hereinafter abbreviated to Z, Bz, Bs, Ts, respectively). The corresponding chlorides (e.g., benzyloxycarbonyl chloride, benzoyl chloride, etc.) and optically active amino acids are subjected to Schotten-Baumann reaction to produce these materials easily with high yield.

The optically active Asp and Glu, raw materials for resolving agents, may be either the D- or L-isomer and should be selected depending on the objective optical isomer, α-arylalkylamine. Among them, L-Asp and Glu are industrially produced by conventional methods known to those of ordinary skill in the art, with ease and at low cost by an enzymatic process or a fermentation process.

The optically active resolving agent is enriched in one of two possible enantiomeric species. Preferably, the optically active resolving agent contains only a single enantiomer, however, the present invention allows for the use of an optically active resolving agent, which contains minor amounts of the second of two enantiomeric species. Preferably, the optically active resolving agent contains an enantiomeric ratio of major enantiomer to minor enantiomer of $\geq 5:1$, more preferably $\geq 10:1$, even more preferably $\geq 20:1$, and most preferably is a single enantiomer.

The alkyl group of the α-arylalkylamine are $C_{1-6}$ alkyl includes, for example, ethyl, n-propyl, n-butyl, i-butyl, etc. Aryl group includes, for example, phenyl, $C_{1-6}$ alkyl-substituted phenyl, naphthyl, etc.

The preferred solvent used includes, for example, water or a hydrophilic organic solvent (e.g., alcohols such as methanol, ethanol; ketones such as acetone, methylethylketone; ethers such as tetrahydrofuran, dioxane; acetonitrile, N,N-dimethylformamide, N,N-dimethylsulfoxide), or a mixture thereof.

The temperature at which N-acyl-Asp or Glu and α-arylalkylamine are mixed is typically not higher than the boiling point of the solvent. Generally, it is in the range from 0° C. to 100° C., preferably from 0° C. to 80° C. The crystallization temperature is desirably not higher than 60° C. to obtain high yield.

The amount of the resolving agent used, i.e., optically active N-acyl-Asp or Glu, is generally 0.2 to 4 mole, desirably 0.3 to 1.5 mole based on 1 mole of racemic α-arylalkylamine.

In some cases, the objective optical isomer of the amine is crystallized as an almost insoluble salt with N-acyl-Asp or Glu to remove the other optical isomer of the amine as an extremely soluble hydrochloride salt in a mother liquor. A method wherein optically active N-acyl-Asp or Glu, as well as acid such as hydrochloric acid, are added to an optically impure amine to crystallize is economical.

The present invention is not particularly limited with respect to the enantiomeric purity of the α-arylalkylamine. However, the optically impure α-arylalkylamine to be resolved should preferably not be a equivalent mixture of R- and S-isomers (i.e racemic). A mixture containing one optical isomer, in a greater amount than the other may be used. Preferably, the α-arylalkylamine to be resolved, contains the two enantiomers in a ratio of from 1.0 to 3.0:1, more preferably from 1.1 to 2.0:1, and most preferably from 1.5 to 1.8:1.

If needed, the diastereomeric salts obtained by crystallization may be, for example, recrystallized to further improve optical purity of the optically active amine.

By crystallization and optional recrystallization, a single diastereomeric salt can be obtained in a diastereomeric excess (de) of ≧15%, preferably ≧20% de, more preferably ≧50% de, even more preferably ≧75% de and most preferably ≧90% de.

In this way, the objective diastereomer salts are obtained, which may be decomposed by suitable methods to isolate the optically active amine and resolving agent.

The methods for decomposition of the diastereomer salts are optional. For example, an aqueous solution containing the diastereomeric salts is treated with alkali, extracted with a suitable organic solvent to separate the optically active amine and water, then the organic solvent is removed to obtain the optically active amine. Alternatively, the aqueous phase, after extraction of the amine is acidified, extracted with a suitable organic solvent and the organic solvent is removed to isolate the N-acyl-amino acid. Such an N-acyl-amino acid can be recycled as a resolving agent.

By the present method, an optically active α-arylalkylamine can be obtained in an enantiomeric excess (ee) of ≧15%, preferably ≧20% ee, more preferably ≧50% ee, even more preferably ≧75% ee and most preferably ≧90% ee.

Having generally described this invention, a further understanding can be obtained by reference to certain specific examples which are provided herein for purposes of illustration only and are not intended to be limiting unless otherwise specified.

The optical purity of α-arylalkylamine was analyzed using optically active HPLC column (Crown pack CR (+)).

EXAMPLE 1

To a solution of Bz-L-Glu (0.30 g, 1.19 mmol) in water (4 ml) was added (S)-α-phenylethylamine (0.15 g, 1.25 mmol), and allowed to stand in a refrigerator overnight. The separated crystals were filtered by suction. The crystals were washed with a small amount of chilled water, then dried under reduced pressure. Weight of the crystal, 0.38 g. mp. 181.5°–183.7° C. The results of HPLC analysis showed that the crystals contained equimolar Bz-L-Glu and (S)-α-phenylethylamine.

EXAMPLE 2

The salts shown in Table 2 were prepared in the same manner as in Example 1.

TABLE 2

| N-Acyl-amino acid· α-arylalkylamine salt | Melting Point (°C.) |
|---|---|
| Z-L-Asp· (S)-α-phenylethylamine | 136.0–138.0 |
| Z-L-Asp· (S)-α-phenylpropylamine | 160.5–162.0 |
| Bz-L-Asp· (S)-α-phenylethylamine | 119.5–(decomp.) |
| Bz-L-Asp· (S)-α-phenylpropylamine | 136.0–(decomp.) |
| Bs-L-Asp· (S)-α-phenylpropylamine | 149.0–150.6 |
| Ts-L-Asp· (S)-α-phenylethylamine | 156.5–160.0 |
| Z-L-Glu· (S)-α-phenylethylamine | 126.0–131.5 |
| Bz-L-Glu· (S)-α-phenylethylamine | 181.5–183.7 |
| Bs-L-Glu· (S)-α-phenylethylamine | 184.4–185.7 |
| Bs-L-Glu· (S)-α-phenylpropylamine | 156.4–157.5 |
| Ts-L-Glu· (S)-α-phenylethylamine | 166.0–166.1 |
| Ts-L-Glu· (S)-α-phenylpropylamine | 169.5–170.4 |
| Z-L-Asp· (R)-α-phenylethylamine | 142.0–144.5 |
| Bz-L-Asp· (R)-α-phenylethylamine | 130.5–138.5 |
| Bz-L-Asp· (R)-α-phenylpropylamine | 176.3–179.5 |
| Bz-L-Glu· (R)-α-phenylethylamine | 174.0–176.0 |
| Bs-L-Glu· (R)-α-phenylethylamine | 183.5–185.0 |
| Bs-L-Glu· (R)-α-phenylpropylamine | 142.0–143.0 |
| Ts-L-Glu· (R)-α-phenylethylamine | 188.5–191.0 |
| Ts-L-Glu· (R)-α-phenylpropylamine | 173.0–176.0 |

EXAMPLE 3

Z-L-Asp (2.67 g, 10 mmol) was dissolved in methanol (10 ml), to which was added (RS)-α-phenylpropylamine (1.35 g, 10 mmol) dissolved in methanol (5 ml). After stirring at room temperature overnight, the separated crystals were filtered by suction. Weight of crystals, 1.64 g. The result of HPLC analysis showed that the crystals contained 1.07 g (4.01 mmol) of Z-L-Asp, 0.51 g (3.79 mmol) of (S)-α-phenylpropylamine, 0.04 g (0.29 mmol) of (R)-α-phenylpropylamine. Yield of S-amine, 75.8% (based on the charged S-amine). Optical purity, 85.8% ee.

EXAMPLE 4

Z-L-ASp (3.95 g, 14.81 mmol) was heated and dissolved in water (100 ml), to which was added (RS)-α-phenylpropylamine (2.00 g, 14.81 mmol). After stirring at room temperature overnight, the separated crystals were filtered by suction. Weight of wet crystals, 3.55 g. The result of HPLC analysis showed that the crystals contained 2.01 g (7.52 mmol) of Z-L-Asp, 0.91 g (6.74 mmol) of (S)α-phenylpropylamine, 0.14 g, (1.03 mmol) of (R)-α-phenylpropylamine. Yield of S-amine, 91.0% (based on the charged S-amine). Optical purity, 73.5% ee.

EXAMPLE 5

(RS)-α-Phenylpropylamine (135.0 g, 1.0 mol) and Z-L-Asp (133.5 g, 0.5 mol) were added to water (500 ml) and heated at 60° C. 2.5 N-HCl (200 ml, 0.5 mol) was added to the solution over 6 hours. After stirring at room temperature overnight, the separated crystal was filtered by suction. Weight of wet crystals, 235.7 g. The result of HPLC analysis showed that the crystals contained 122.5 g (0.46 mol) of Z-L-Asp, 60.95 g (0.45 mol) of (S)-α-phenylpropylamine, 5.00 g (0.037 mol) of (R)-α-phenylpropylamine. Yield of S-amine, 90.3% (based on the charged S-amine). Optical purity, 84.8% ee.

The wet crystals (200 g) were added to water (6,200 ml) and heated at 60° C. to dissolve. After a small amount of insolubles were removed by filtration, the filtrate was recrystallized while stirring at room temperature overnight. The separated crystals were filtered by suction. Weight of wet crystals, 128.7 g. The result of HPLC analysis showed that the crystal contained 42.1 g of (S)-α-phenylpropylamine and 0.28 g of (R)-α-phenylpropylamine. Yield of recrystallization of S-amine, 81.4%. Optical purity, 98.7% ee.

The crystals (120 g) were dispersed in water (300 ml), to which was added 25% NaOH to adjust pH of the solution to 12. The solution was extracted with ether (2×500 ml). The ether layers were collected, washed with saturated brine, then dried over anhydrous sodium sulfate. Sodium sulfate was removed by filtration, and ether was distilled off from the resulting filtrate under reduced pressure to give 38.2 g of (S)-α-phenylpropylamine as an oil. Yield based on S-amine in the starting (RS)-amine was 71.5%.

EXAMPLE 6

(RS)-α-Phenylethylamine (0.964 g, 7.97 mmol) and Bz-L-Glu (1.00 g, 3.99 mmol) were added to water (13 ml). 35% HCl (0.35 ml, 3.96 mmol) was added to this solution. After stirring at room temperature overnight, the separated crystals were filtered by suction. Weight of wet crystals, 1.27 g. The result of HPLC analysis showed that the crystals contained 0.84 g (3.35 mmol) of Bz-L-Glu, 0.391 g (3.23 mmol) of (S)-α-phenylethylamine and 0.018 g (0.14 mmol) of (R)-α-phenylethylamine. Yield of S-amine, 81.1% (based on the charged S-amine). Optical purity, 91.5% ee.

EXAMPLE 7

(RS)-α-Phenylpropylamine (0.92 g, 6.81 mmol) and Ts-L-Glu (1.02 g, 3.39 mmol) were added to water (13 ml). 35% HCl (0.3 ml, 3.39 mmol) was added to this solution. After stirring at room temperature overnight, the separated crystals were filtered by suction. Weight of wet crystals, 2.32 g. The result of HPLC analysis showed that the crystals contained 0.958 g (3.18 mmol) of Ts-L-Glu, 0.284 g (2.10 mmol) of (R)-α-phenylpropylamine and 0.155 g (1.15 mmol) of (S)-α-phenylpropylamine. Yield of R-amine, 61.8% (based on the charged R-amine). Optical purity, 29.5% ee.

EXAMPLE 8

(RS)-α-Phenylethylamine (6.05 g, 50 mmol) and Z-L-Asp (6.68 g, 25 mmol) were added to water (37 ml). 144 N-HCl (17.4 ml, 25 mmol) was added to this solution. After stirring at room temperature for 3.5 hours, the separated crystals were filtered by suction. Weight of wet crystals, 8.11 g. The result of HPLC analysis showed that the crystals contained 3.38 g (12.66 mmol) of Z-L-Asp, 0.93 g (7.69 mmol) of (R)-α-phenylethylamine and 0.65 g (5.36 mmol) of (S)-(α-phenylethylamine. Yield of R-amine, 30.8% (based on the charged R-amine). Optical purity, 17.9% ee.

EXAMPLE 9

(RS)-α-Phenylethylamine (4.84 g, 40 mmol) and Ts-L-Asp (5.74 g, 20 mmol) were added to water (30 ml). 2.58 N-HCl (7.76 ml, 20 mmol) was added to this solution. After stirring at room temperature for 3.5 hours, the separated crystals were filtered by suction. Weight of wet crystals, 5.60 g. The result of HPLC analysis showed that the crystals contained 3.92 g (13.65 mmol) of Ts-L-Asp, 0.98 g (8.09 mmol) of (S)-α-phenylethylamine and 0.54 g (4.47 mmol) of (R)-α-phenylethylamine. Yield of S-amine, 40.5% (based on the charged S-amine). Optical purity, 28.8% ee.

EXAMPLE 10

(RS)-α-Phenylpropylamine (6.75 g, 50 mmol) and Bs-L-Asp (6.83 g, 25 mmol) were added to water (35 ml). 3.05 N-HCl (8.2 ml, 25 mmol) was added to this solution. After stirring at room temperature overnight, the separated crystals were separated by suction filtration. Weight of wet crystals, 9.36 g. The result of HPLC analysis showed that the crystals contained 4.90 g (17.96 mmol) of Bs-L-Asp, 1.97 g (14.62 mmol) of (S)-α-phenylpropylamine and 0.52 g (3.82 mmol) of (R)-α-phenylpropylamine. Yield of S-amine. Optical purity, 58.6% ee.

According to the present invention, optical resolution of α-arylalkylamine can be conducted using a cheap material as a resolving agent by simple operation at high yield.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for optical resolution, comprising:

i) mixing an optically active N-acyl-aspartic acid or an optically active N-acyl-glutamic acid and an optically impure α-arylalkylamine in a solvent to form the corresponding diastereomeric salts; and ii) separating the two diastereomeric salts utilizing differences in solubility, wherein the aryl in said α-arylalkylamine is selected from the group consisting of phenyl, $C_{1-6}$ alkyl-substituted phenyl and naphthyl, and wherein the acyl group of said N-acyl-aspartic acid or N-acyl-glutamic acid is selected from the group consisting of benzyloxycarbonyl, benzoyl, benzenesulfonyl or p-toluenesulfonyl.

2. The process of claim 1, further comprising decomposing said separated diastereomeric salts into an optically active α-arylalkylamine and said optically active N-acyl-aspartic acid or glutamic acid.

* * * * *